(12) United States Patent
Buettner

(10) Patent No.: US 8,850,640 B2
(45) Date of Patent: Oct. 7, 2014

(54) PATIENT SUPPORT TABLE, MEDICAL APPARATUS WITH A PATIENT SUPPORT TABLE, AND METHOD FOR OPERATING A PATIENT SUPPORT TABLE

(75) Inventor: Thorsten Buettner, Pretzfeld (DE)

(73) Assignee: Siemens Aktiengesellschaft, Munich (DE)

( * ) Notice: Subject to any disclaimer, the term of this patent is extended or adjusted under 35 U.S.C. 154(b) by 49 days.

(21) Appl. No.: 13/527,874

(22) Filed: Jun. 20, 2012

(65) Prior Publication Data

US 2012/0317724 A1 Dec. 20, 2012

(30) Foreign Application Priority Data

Jun. 20, 2011 (DE) .......................... 10 2011 077 797

(51) Int. Cl.
| | |
|---|---|
| A47B 13/00 | (2006.01) |
| A61B 5/00 | (2006.01) |
| A61B 6/00 | (2006.01) |
| A61B 6/03 | (2006.01) |
| A61B 6/04 | (2006.01) |
| A61B 5/055 | (2006.01) |

(52) U.S. Cl.
CPC .............. *A61B 6/0407* (2013.01); *A61B 5/7475* (2013.01); *A61B 6/467* (2013.01); *A61B 6/03* (2013.01); *A61B 6/0457* (2013.01); *A61B 5/0555* (2013.01)
USPC .......................................... 5/601; 5/81.1 HS

(58) Field of Classification Search
USPC ......... 5/601, 81.1 HS, 81.1 R, 600, 905, 943; 378/209
See application file for complete search history.

(56) References Cited

U.S. PATENT DOCUMENTS

| | | | | |
|---|---|---|---|---|
| 6,460,206 | B1 * | 10/2002 | Blasche et al. ..................... 5/601 |
| 7,308,075 | B2 * | 12/2007 | Barkow et al. ................... 378/20 |
| 2005/0052426 | A1 * | 3/2005 | Hagermoser et al. ......... 345/173 |
| 2006/0034421 | A1 | 2/2006 | Barkow et al. |
| 2007/0229477 | A1 * | 10/2007 | Ludwig ........................ 345/173 |
| 2008/0194942 | A1 * | 8/2008 | Cumpson et al. ............. 600/415 |

FOREIGN PATENT DOCUMENTS

EP 2 204 909 A1 7/2010

\* cited by examiner

*Primary Examiner* — Robert G Santos
*Assistant Examiner* — Richard G Davis
(74) *Attorney, Agent, or Firm* — Schiff Hardin LLP

(57) ABSTRACT

A patient support table has a patient support plate adjustable along at least one axis to support a patient thereon, and at least one touch-sensitive input device, wherein sweeping over or marking a segment of the at least one touch-sensitive input device by a user is translated into an adjustment of the patient support plate along the at least one axis. A medical apparatus includes such a patient support table, and in a method to adjust the patient support plate of the patient support table, appropriate interaction of a user with the touch-sensitive input device effects the adjustment of the support plate along the at least one axis.

14 Claims, 2 Drawing Sheets

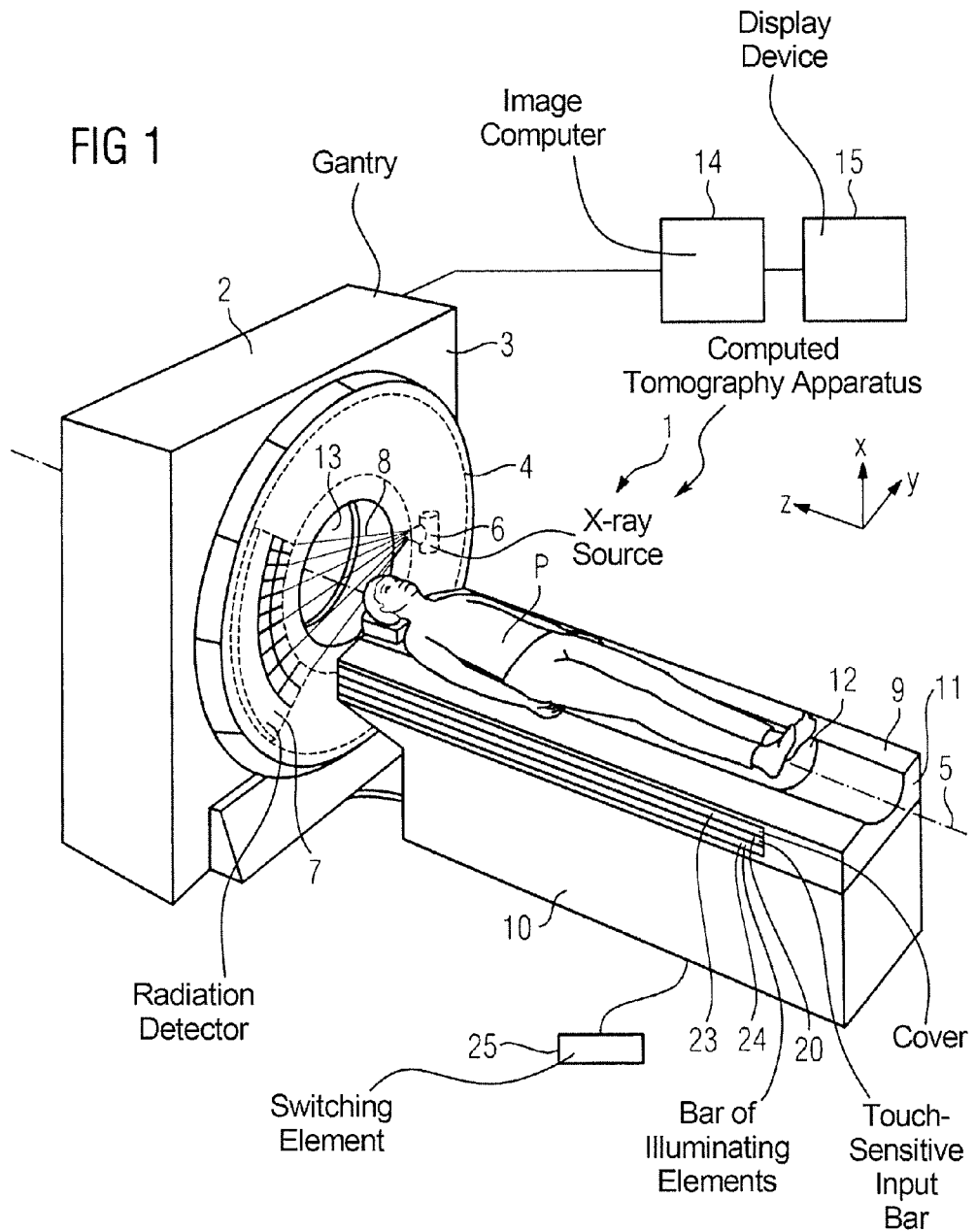

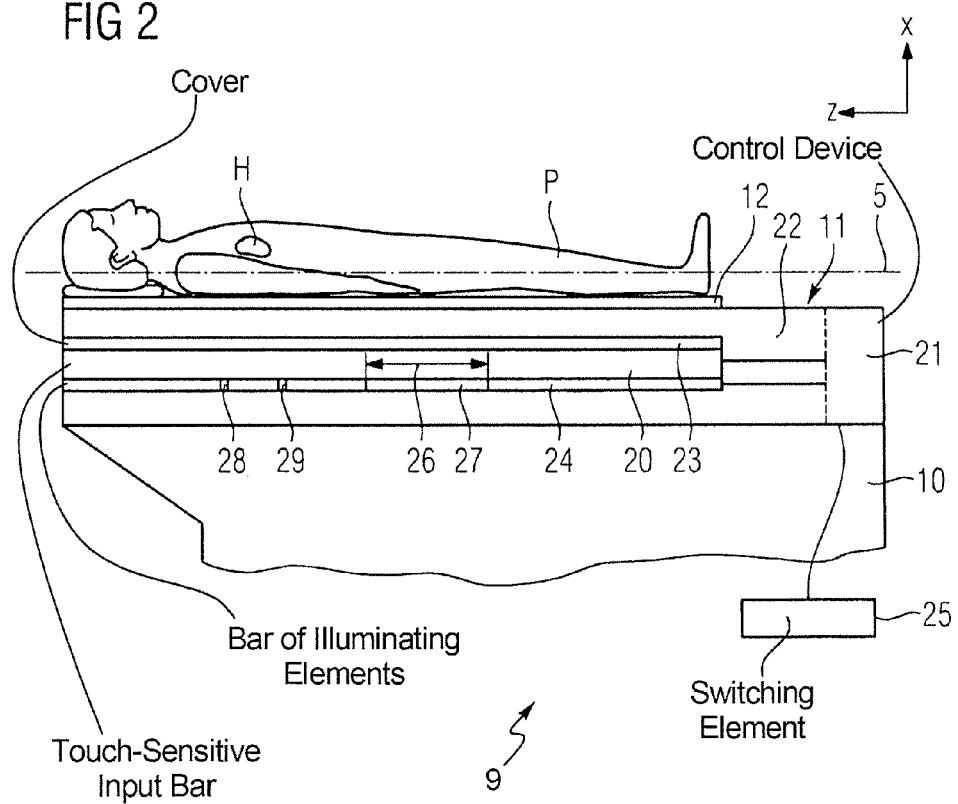

PATENT SUPPORT TABLE, MEDICAL APPARATUS WITH A PATIENT SUPPORT TABLE, AND METHOD FOR OPERATING A PATIENT SUPPORT TABLE

BACKGROUND OF THE INVENTION

1. Field of the Invention

The present invention concerns a patient support table of the type having a patient support plate for a patient that can be adjusted along at least one axis, and an operating device to make or to initiate the adjustment of the patient support plate. The invention moreover concerns a medical apparatus that has such a patient support table. The invention furthermore concerns a method for operating a patient support table, in particular to adjust the patient support plate of the patient support table.

2. Description of the Prior Art

Patient support tables, in particular patient support tables for imaging medical apparatuses such as computed tomography apparatuses or magnetic resonance apparatuses, normally have a patient support plate that can be moved along, or alongside, an axis relative to a base of the table, for example in order to bring a patient into an image acquisition region of the imaging medical apparatus with the patient support plate after positioning the patient on the patient support plate.

To move or adjust the patient support plate, the patient support table can have an operating device that includes a control lever like a joystick, for example. Both the direction of the adjustment and the speed of the adjustment can be set with the control lever. The adjustment movement itself takes place by an actuator of the patient support table that is connected with the control lever via control means and that adjusts the patient support plate relative to the base. If the control lever is arranged directly at the patient support plate, it advantageously influences the operator ergonomics since the operator experiences the adjustment movement upon operation of the control lever and in this way receives a direct feedback with regard to the adjustment movement. In order to be able to achieve this advantage, however, the control lever must be arranged at a location at the patient support plate at which the control lever interferes with the mounting and dismounting of the patient.

Alternatively, the patient support plate can be manually adjusted relative to the base of the patient support table. For this purpose, for example, the actuator can be separated from the patient support plate by a coupling. Depending on the embodiment, however, relatively large forces can be necessary for the adjustment.

SUMMARY OF THE INVENTION

An object of the present invention is to equip a patient support table and a medical apparatus with a patient support table with an alternative operating device. A further object is to provide a method based on such an alternative operating device for the patient support table.

According to the invention, this object is achieved by a patient support table having a patient support plate that is adjustable along at least one axis to support a patient, and at least one touch-sensitive input device, wherein sweeping over or marking a segment of the at least one touch-sensitive input device (with a finger of a user, for example) is translated into an adjustment of the patient support plate along the at least one axis.

The touch-sensitive input device is advantageously connected with at least one control device (for example of the patient support table) that registers the length of the segment or region of the touch-sensitive input device that is contacted, swept over or marked, and registers the direction of the sweep or the marking, and controls an actuator (for example an electrical actuator) of the patient support table such that the patient support plate is adjusted accordingly.

The adjustment of the patient support plate can take place with practically no effort in this manner, and without a direct force imparted by the user to the patient support plate. If the user wishes to position the patient support plate exactly, with a finger placed on the touch-sensitive input device he or she makes a slow movement of that finger until the patient support plate is positioned as desired, for example. The patient support plate also can be adjusted relatively quickly by repeated fast sweeping over segments or regions of the touch-sensitive input device.

The advantage of the touch-sensitive input device relative to the control lever is that the touch-sensitive input device (which is designed as a flat operating element) interferes with neither the mounting nor the dismounting of a patient onto or from the patient support plate.

The translation ratio of the length of the swept or marked segment or region of the touch-sensitive input device, to the length or distance of the adjustment of the patient support plate that results from this, is advantageously 1:1.

In an embodiment of the invention, the at least one touch-sensitive input device is a touch-sensitive, two-dimensional screen (for example in the form of a touchscreen or a touch pad) or a touch-sensitive, one-dimensional input bar that can be designated as a "touch bar".

According to a variant of the invention, the at least one touch-sensitive input bar is designed as a ribbon controller. In contrast to a touchscreen or touch pad, the ribbon controller is only one-dimensional (as already noted). By touching or sweeping along the ribbon controller, signals are generated that are translated into a corresponding adjustment movement of the patient support plate.

According to a further variant of the invention, the at least one touch-sensitive input device has resistive, capacitive and/or inductive sensors. Resistive sensors are preferred for the provided use of the patient support table since this way an operation of the touch-sensitive input device is also possible with gloves (as are frequently worn in a medical environment).

In a further embodiment of the invention, the length of the at least one touch-sensitive input device corresponds to the maximum adjustment range of the patient support plate along the at least one axis. This accommodates an intuitive operation or adjustment of the patient support plate by a user according to the preferred translation ratio of 1:1.

In another embodiment of the invention, the patient support table has a support element that supports the patient support plate and relative to which the patient support plate is adjustable along the at least one axis, and the at least one touch-sensitive input device is arranged on the support element. The support element is normally arranged on a base of the patient support table.

In a further embodiment of the invention, the support element has a top side and two longitudinal sides or two lateral surfaces, and the top side at least partially has the patient support plate thereon and the at least one touch-sensitive input device is arranged on at least one of the two sides or lateral surfaces. In order to be able to operate the patient support table from both sides, a touch-sensitive input device can also be arranged on each side, or on each of the two lateral surfaces. The arrangement of a touch-sensitive input device on one side, or on one lateral surface has the advantage that a patient cannot inadvertently operate the touch-sensitive input device without additional measures upon mounting or dismounting from the patient support plate.

The at least one touch-sensitive input device arranged on the at least one side or lateral surface is advantageously recessed relative to the surface of the at least one side or is provided on its top side with a covering or protective strip. Protection against an unwanted operation by a patient (due to an arm or leg of a patient that is hanging down) is increased again in this way.

In another embodiment of the invention, at least one illuminating element is associated with the at least one touch-sensitive input device. The at least one illuminating element can be at least one LED (Light Emitting Diode), at least one light-emitting film and/or at least one laser. In the case of LEDs, at least one bar composed of a number of LEDs that begins and ends with the touch-sensitive input device (thus has the same length) is associated with the touch-sensitive input device. A light-emitting film or a number of light-emitting film elements can be similarly associated with the touch-sensitive input device. If the at least one illuminating element is designed as at least one laser, there is the possibility of producing projections of laser light relative to the touch-sensitive input device and/or the patient support plate, which projections are correlated with inputs made via said touch-sensitive input device.

Given functional coupling of the illuminating elements with the touch-sensitive input device, in the operation of the touch-sensitive input device an optical feedback can accordingly be provided to the operator with such an illuminating element or with such illuminating elements.

According to another embodiment of the invention, the patient support table has at least one switching element with which various operating modes can be selected for operation of the patient support table. Such a switching element can be executed as a foot switch or even as a manual switch, for example. In the case of a manual switch, this is advantageously arranged on the support element in the region of the touch-sensitive input device.

In another embodiment of the invention, in a specific selected operating mode of the patient support table—in particular in combination or in operation with an imaging medical apparatus—a start point and an end point for a region in which image information should be acquired with an imaging apparatus can be established with the touch-sensitive input device relative to the patient support plate. If the patient support table is part of a computed tomography apparatus (for example), the scan region for an examination of a body segment of a patient can be established in this way. According to variants of the invention, the start point can be identified by a first color with the at least one illuminating element, and the end point can advantageously be identified by a second color that is different than the first.

The above object also is achieved in accordance with the invention by a medical apparatus that has a patient support tables as described in the preceding. The medical apparatus is advantageously a computed tomography apparatus, an x-ray apparatus (in particular a C-arm x-ray apparatus), a magnetic resonance apparatus, a PET apparatus, a SPECT apparatus or a radiation therapy apparatus.

The above object also is achieved in accordance with the invention by a method to adjust a patient support plate of a patient support table having a touch-sensitive input device along at least one axis, in which method the sweeping over or marking of a segment of the at least one touch-sensitive input device is registered, and in which the patient support plate is adjusted accordingly along the at least one axis based on the registered swept or marked segment of said at least one touch-sensitive input device.

BRIEF DESCRIPTION OF THE DRAWINGS

FIG. 1 shows a computed tomography apparatus embodying a patient support table in accordance with the invention.

FIG. 2 shows a part of the patient support table of the computed tomography apparatus of FIG. 1, in a side view.

DESCRIPTION OF THE PREFERRED EMBODIMENTS

Identical or functionally identical elements in the figures are provided throughout with the same reference characters. The representations in the figures are schematic and not necessarily true to scale. In the exemplary embodiment of the invention, the medical apparatus is a computed tomography apparatus 1, which is discussed in the following without limitation of the generality only insofar as is deemed necessary to understand the invention.

The computed tomography apparatus 1 shown in FIG. 1 has a gantry 2 with a stationary part 3 and with a part 4 that is rotatable around a system axis 5. In the exemplary embodiment of the invention, the rotatable part 4 has an x-ray system which comprises an x-ray source 6 and an x-ray detector 7 that are arranged opposite one another on the rotatable part 4. In the operation of the computed tomography apparatus 1, x-ray radiation 8 emanates from the x-ray source 6 in the direction of the x-ray detector 7, penetrates a measurement subject and is detected by the x-ray detector 7 in the form of measurement data or measurement signals.

The computed tomography apparatus 1 furthermore has a patient support table 9 to bear a patient P to be examined. In the exemplary embodiment of the invention, the patient support table 9 has a bed base 10 as well as a support element 11 for a patient support plate 12 provided to actually support the patient P. The patient support plate 12 is adjustable relative to the support element 11 and relative to the bed base 10 in the directions of the system axis 5 (the z-axis) shown in FIG. 1, such that the support element 11 together with the patient P can be introduced into the opening 13 of the gantry 2 to acquire x-ray projections of the patient P (in a spiral scan, for example). The computational processing of the x-ray projections acquired with the x-ray system, namely the reconstruction of slice images, 3D images or a 3D data set takes place with an image computer 14 of the computed tomography apparatus 1 based on the measurement data or the measurement signals of the x-ray projections. The reconstructed slice images or 3D images can be shown on a display device 15.

For a user-controlled adjustment of the patient support plate 12 along the system axis 5 or the z-axis relative to the support element 11, the patient support table 9 has a touch-sensitive input device that is shown in detail in FIG. 2. This input device, in the shown embodiment, is a touch-sensitive input bar 20 with one-dimensional input capability in the case of the present exemplary embodiment of the invention. The touch-sensitive input bar 20 can be designed with capacitive, inductive and/or resistive sensors with which the touching or the sweeping over a segment or a region of the touch-sensitive input bar 20 (with a finger of a user, for example) is registered. Corresponding signals are generated by the sensors depending on the touched or swept segment, which signals are supplied to a control device 21 (shown simplified and only schematically in FIG. 2), which can be a computer. The control device 21 can include one or more controllers of the computer tomography apparatus 1 and/or of the patient support table 9 that can interact to mechanically adjust (move) the patient support plate 12.

The sensors of the touch-sensitive input bar 20 are advantageously resistive sensors so that the adjustment of the patient support plate 12 can take place via operation of the touch-sensitive input bar 20, even with gloves.

In the exemplary embodiment of the invention, the touch-sensitive input bar 20 is moreover a ribbon controller as is commercially available and used in the field of music. The operation or the adjustment of the patient support plate 12 is possible very precisely with such a ribbon controller since the sensors of said ribbon controller normally operate very precisely and sensitively so that an activation takes place even upon a light placement of a finger on the touch-sensitive input bar 20.

The control device 21 interacts with a known drive or actuating unit (not shown in Figures) of the patient support table 9, meaning that the control device 21 controls the drive unit such that the patient support plate 12 is adjusted corresponding to the operation of the touch-sensitive input bar 20. In the case of the present exemplary embodiment of the invention, the translation ratio is 1:1, meaning that the length of the adjustment of the patient support plate 12 corresponds to the length of the segment of the touch-sensitive input bar 20 that is swept over with the finger. The total length of the touch-sensitive input bar 20 advantageously corresponds to the maximum adjustment range of the patient support plate 12 relative to the support element 11 out of its original position, by which is meant the position in which no adjustment or, respectively, projection of the patient support plate 12 has occurred relative to the support element 11. The selected translation ratio as well as the selected total length of the touch-sensitive input bar 20 accommodates an intuitive operation by a user.

The control device 21 also detects in which direction the touch-sensitive input bar 20 is swept over so that the adjustment of the patient support plate 12 takes place in the same direction. The drive unit can be an electrical drive in the form of an electric motor, for example.

Since the touch-sensitive input bar 20 or, respectively, the ribbon controller 20 is very sensitive to touch, a protection against random, unwanted contact (in particular by a patient) is necessary. For this reason the touch-sensitive input bar 20 is arranged on the side or the lateral surface 22 of the support element 11 at which it is nevertheless still well accessible to a user.

In the present exemplary embodiment of the invention, a covering or protective cover 23 is arranged over the touch-sensitive input bar 20 as an additional measure in order to prevent the touch-sensitive input bar 20 from being activated unintentionally by a hanging arm of a patient, a hanging leg of a patient or hanging medical elements (such as tubes, cannula etc.). Alternatively, the touch-sensitive input bar 20 can be set back relative to (recessed in) the lateral surface 22.

In the exemplary embodiment of the invention, a bar 24 of illuminating elements (which presently are LEDs) is additionally associated with the touch-sensitive input bar 20. Alternatively, the bar 24 can be a commercially available light-emitting film or a plurality of light-emitting film elements which form the bar 24.

The bar 24 of LEDs has the same length as the touch-sensitive input bar 20 and presently serves to illuminate the operation that is made, whereby the user receives an optical feedback. For this the bar 24 of LEDs is connected with the control device 21.

Furthermore, the patient support table 9 has a switching element 25 that, in the case of the present exemplary embodiment of the invention, is designed as a foot switch 25. The foot switch 25 is also connected with the control device 21. In the case of the present exemplary embodiment of the invention, the foot switch 25 additionally serves (among other things) to operate the patient support table 9 in different operating or, respectively, control modes as a component of the computed tomography apparatus 1.

In a first mode activated by the foot switch 25, as already mentioned a corresponding adjustment of the patient support plate 12 relative to the support element 111 in the direction of the system axis 5 at a translation ratio of 1:1 takes place upon touching or sweeping over a segment or a region of the touch-sensitive input bar 20. The segment or region of the touch-sensitive input bar 20 that is influenced by the user is correspondingly illuminated or marked by the bar 24 in this case, meaning that the LEDs of the bar 24 advantageously illuminate below the swept-over region of the touch-sensitive input bar 20 until the adjustment movement has concluded. How the marking of the region 26 by the illumination of the group of LEDs 27 of the bar 24 takes place via sweeping over the region 26 of the touch-sensitive input bar 20 is illustrated in FIG. 2.

A second mode can be activated by the switching element 25, which can be a foot switch. The scan region for an examination of the patient P (thus the region or body segment of the patient P) in which image information of the patient P should be acquired with the computed tomography apparatus 1 thus can be established or identified.

For this purpose, the patient support plate 12 with the patient P thereon is initially brought into a desired initial position. In this operating mode the beginning and the end of what is known as the scan range or the scan region can then be established with the touch-sensitive input bar 20 with direct reference to the body of the patient P that is borne on the patient support plate 12. For this purpose, the touch-sensitive input bar 20 is touched at the point at which the scan should start and at the point at which the scan should end. The start point and the end point thus can be marked accordingly via the bar 24 of LEDs, with the start point being advantageously illuminated with a different color than the end point for the purpose of differentiation.

FIG. 2 illustrates this establishment of the scan range for the examination of the heart H of the patient P. The LED 28 identifies the beginning of the scan range and the LED 29 identifies the end of the scan range. Since the position of the patient support plate 12 relative to the gantry 2 or the x-ray system of the gantry 2 within the computer tomography apparatus 1 is known, the acquisition of x-ray projections of the region of the body that comprises the heart H of the patient P is only started when, in the adjustment of the patient support plate 12 in the course of the scan, the start point indicated by the LED 28 reaches the plane of the image acquisition. The acquisition of x-ray projections ends when the end point indicated by the LED 29 has passed the plane of the image acquisition. The plane of the image acquisition is thereby established in a defined manner by the x-ray source 6 and the x-ray detector 7.

By establishing the start point and end point of the scan range, it can also be equally established whether the scan should take place from the head down toward the body or from the feet up toward the body.

The exemplary embodiment of the invention that is described in the preceding is to be understood only as an example in the following.

The patient support table can also be a component of a different medical apparatus, for example a C-arm x-ray apparatus, a magnetic resonance apparatus, a PET apparatus, a SPECT apparatus or a radiation therapy apparatus.

Furthermore, individual details or components of the patient support table can be designed or, respectively, executed as described in the preceding. For operation on both sides, the patient support table can thus also be provided with a touch-sensitive input bar on both sides. The foot switch and the illuminating elements are optional and do not necessarily need to be present or present together.

At least one laser can also be provided as illuminating means instead of LEDs or light-emitting film. In this case, the bar 24 is advantageously provided as a projection surface or, respectively, projection bar. If the lasers and the touch-sensitive input bar are functionally coupled, the swept region of the touch-sensitive input bar or the start point and end point of a selected scan range etc. (for example) can be illuminated by means of projection of laser light onto the bar 24 depending on operator inputs via the touch-sensitive input bar as described in the preceding.

The touch-sensitive input bar does not need to be executed as a ribbon controller. Moreover, the translation ratio and the total length of the touch-sensitive bar can be chosen differently.

Alternatively, instead of the touch-sensitive input bar a touchscreen or a touchpad can also be present as a touch-sensitive input device.

The control device 21—which, as was already noted, can have multiple controllers—does not necessarily need to be arranged in the patient support table 9. Rather, the control device 21 can also be arranged in the gantry of the computer tomography apparatus 1. If the control device 21 has multiple controllers that interact or are electrically connected with one another to control the adjustment of the patient support plate 12, one or more controllers can be arranged in the gantry and one or more controllers can be arranged in the patient support table 9.

Although modifications and changes may be suggested by those skilled in the art, it is the intention of the inventor to embody within the patent warranted hereon all changes and modifications as reasonably and properly come within the scope of his contribution to the art.

I claim as my invention:

1. A patient support table comprising:
    a table base;
    a patient support plate configured to receive a patient thereon, said patient support plate being movable along at least one axis with respect to said table base;
    a controller configured to operate said patient support plate to cause said patient support plate to move through an adjustment range along said at least one axis;
    at least one touch-sensitive input device connected to said controller, said touch-sensitive input device having a continuous, undivided touch-sensitive field that is co-extensive with said adjustment range, and that is configured to respond to a user interaction with said touch-sensitive field, selected from the group consisting of sweeping over said touch-sensitive field or marking a segment of said touch-sensitive field, by translating said user interaction into a control command to said controller that causes said patient support plate to be moved along said at least one axis in a direction and through a distance indicated by said user interaction with said touch-sensitive field;
    a support element that supports said patient support plate on said patient table to allow said movement along said at least one axis with respect to said table base, and wherein said at least one touch-sensitive input device is mounted on said support element; and
    said support element comprising a top side and two lateral sides, said patent support plate being mounted on at least a portion of said top side of said support element, and said at least one touch-sensitive input device being mounted on at least one of said two lateral sides of said support element.

2. A patient support table as claimed in claim 1 wherein said at least one touch-sensitive input device is selected from the group consisting of a touch-sensitive screen and a touch-sensitive input bar.

3. A patient support table as claimed in claim 1 wherein said at least one touch-sensitive input device is a touch-sensitive input bar configured as a ribbon controller.

4. A patient support table as claimed in claim 1 wherein said at least one touch-sensitive input device comprises sensors that detect said user interaction with said touch-sensitive field, said sensors being selected from the group consisting of resistive sensors, capacitive sensors, and inductive sensors.

5. A patient support table as claimed in claim 1 wherein said at least one touch-sensitive input device input device is recessed into said at least one lateral side of said support element.

6. A patient support table as claimed in claim 1 wherein said at least one touch-sensitive input device has an upper device side that is closest to said top side of said support element, and wherein said patient support table comprises a covering at said top device side of said touch-sensitive input device.

7. A patient support table as claimed in claim 1 wherein said at least one touch-sensitive input device comprises at least one light-emitting element.

8. A patient support table as claimed in claim 7 wherein said at least one light-emitting element is selected from the group consisting of at least one light-emitting diode, at least one light-emitting film, and at least one laser.

9. A patient support table as claimed in claim 1 wherein said controller is configured to operate said patient support plate in a plurality of different operating modes, and comprising at least one switching element that is actuatable to select operation of said patient support plate in a selected one of said different operating modes.

10. A patient support table as claimed in claim 9 wherein said at least one touch-sensitive input device, in at least one of said different operating modes, is configured to designate a start point and an end point of said movement of said patient support table by said user interaction with said at least one touch-sensitive field.

11. A patient support table as claimed in claim 10 wherein said at least one input device comprises at least one light-emitting element, and wherein said start point and said end point are identified by said at least one light-emitting element.

12. A patient support table as claimed in claim 11 wherein said start point is identified by a first color of light emitted by said at least one light-emitting element and wherein said end point is identified by a second color of light, different from said first color of light, emitted by said at least one light-emitting element.

13. A patient support table as claimed in claim 1 comprising, in said controller, translating said distance indicated by said user interaction with said touch-sensitive input device into a distance that said controller moves said patient support table according to a 1:1 ratio.

14. A patient support table comprising:
    a table base;

a patient support plate configured to receive a patient thereon, said patient support plate being movable along at least one axis with respect to said table base;

a controller configured to operate said patient support plate to cause said patient support plate to move through an adjustment range along said at least one axis;

at least one touch-sensitive input device connected to said controller, said touch-sensitive input device having a continuous, undivided touch-sensitive field that is co-extensive with said adjustment range, and that is configured to respond to a user interaction with said touch-sensitive field, selected from the group consisting of sweeping over said touch-sensitive field or marking a segment of said touch-sensitive field, by translating said user interaction into a control command to said controller that causes said patient support plate to be moved along said at least one axis in a direction and through a distance indicated by said user interaction with said touch-sensitive field;

said controller being configured to operate said patient support plate in a plurality of different operating modes, and comprising at least one switching element that is actuatable to select operation of said patient support plate in a selected one of said different operating modes;

said at least one touch-sensitive input device, in at least one of said different operating modes, is configured to designate a start point and an end point of said movement of said patient support table by said user interaction with said at least one touch-sensitive field;

said at least one input device comprising at least one light-emitting element, and wherein said start point and said end point are identified by said at least one light-emitting element; and said start point being identified by a first color of light emitted by said at least one light-emitting element and wherein said end point being identified by a second color of light, different from said first color of light, emitted by said at least one light-emitting element.

\* \* \* \* \*